United States Patent [19]
Skotnicki et al.

[11] Patent Number: 5,508,286
[45] Date of Patent: Apr. 16, 1996

[54] RAPAMYCIN AMIDINO CARBAMATES

[75] Inventors: Jerauld S. Skotnicki, Allentown, N.J.;
Yvette L. Palmer, Newtown, Pa.

[73] Assignee: American Home Products Corporation, Madison, N.J.

[21] Appl. No.: 450,771

[22] Filed: May 24, 1995

Related U.S. Application Data

[62] Division of Ser. No. 259,763, Jun. 14, 1994, Pat. No. 5,463,048.

[51] Int. Cl.$^6$ ............ A61K 31/395; C07D 498/16
[52] U.S. Cl. ............................ 514/291; 540/456
[58] Field of Search ............ 540/456; 514/291

[56] References Cited

U.S. PATENT DOCUMENTS

| | | | |
|---|---|---|---|
| 3,929,992 | 12/1975 | Sehgal et al. | 540/456 |
| 3,993,749 | 11/1976 | Sehgal et al. | 540/456 |
| 4,316,885 | 2/1982 | Rakhit | 540/456 |
| 4,375,464 | 3/1983 | Sehgal et al. | 540/456 |
| 4,401,653 | 8/1983 | Eng | 540/456 |
| 4,650,803 | 3/1987 | Stella et al. | 540/456 |
| 4,885,171 | 12/1989 | Surendra et al. | 540/456 |
| 5,023,262 | 6/1991 | Caufield et al. | 540/456 |
| 5,023,263 | 6/1991 | Von Burg | 540/456 |
| 5,023,264 | 6/1991 | Caufield et al. | 540/456 |
| 5,078,999 | 1/1992 | Warner et al. | 540/456 |
| 5,080,899 | 1/1992 | Sturm et al. | 540/456 |
| 5,091,389 | 2/1992 | Ondeyka et al. | 540/456 |
| 5,100,883 | 3/1992 | Schiehser | 540/456 |
| 5,100,899 | 3/1992 | Calne | 540/456 |
| 5,102,876 | 4/1992 | Caufield | 540/456 |
| 5,118,677 | 6/1992 | Caufield | 540/456 |
| 5,118,678 | 6/1992 | Kao et al. | 540/456 |
| 5,120,842 | 6/1992 | Failli et al. | 540/456 |
| 5,130,307 | 7/1992 | Failli et al. | 540/456 |
| 5,138,051 | 8/1992 | Hughes et al. | 540/456 |
| 5,151,413 | 9/1992 | Caufield et al. | 540/456 |
| 5,169,851 | 12/1992 | Hughes et al. | 540/456 |
| 5,177,203 | 1/1993 | Failli et al. | 540/456 |
| 5,194,447 | 3/1993 | Kao | 540/456 |
| 5,221,670 | 6/1993 | Caufield | 540/456 |
| 5,233,036 | 8/1993 | Hughes | 540/456 |
| 5,260,300 | 11/1993 | Hu | 540/456 |
| 5,262,423 | 11/1993 | Kao | 540/456 |
| 5,286,730 | 2/1994 | Caufield et al. | 540/456 |
| 5,286,731 | 2/1994 | Caufield et al. | 540/456 |
| 5,302,584 | 4/1994 | Kao et al. | 540/456 |

FOREIGN PATENT DOCUMENTS

| | | | |
|---|---|---|---|
| 507555A1 | 7/1992 | European Pat. Off. | 540/456 |
| WO9113899 | of 0000 | WIPO | 540/456 |

OTHER PUBLICATIONS

Commonly owned U.S. Patent Application SN 08/259,763 filed Jun. 14, 1994.
Commonly owned U.S. Patent Application SN 08/160,984 filed Dec. 1, 1993.

Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11 (pt. 2):197 (1992).
Stepkowski, S. M., Transplantation Proc. 23:507 (1991).

Primary Examiner—Robert T. Bond
Attorney, Agent, or Firm—Arnold S. Milowsky

[57] ABSTRACT

A compound of the structure

[structure of rapamycin derivative shown with OR, OMe, OR$^1$, MeO, OMe, HO, and other substituents]

wherein R and R$^1$ are each, independently, hydrogen, or $$-\overset{O}{\underset{\|}{C}}-\underset{\underset{R^2}{|}}{N}-\overset{R^4}{\underset{\|}{C}}=N-R^3;$$

R$^2$ and R$^3$ are each, independently, hydrogen, alkyl, alkenyl, alkynyl, —CO$_2$R$^5$, —COR$^5$, —CN, —NO$_2$, —SO$_2$R$^5$, —SO$_3$R$^5$, —OR$^5$, —SR$^5$, or Ar;
R$^4$ is hydrogen, alkyl, alkenyl, alkynyl, —CF$_3$, —NR$^5$R$^6$, —CO$_2$R$^5$, —COR$^5$, CONR$^5$R$^6$, —NO$_2$, halogen, —OR$^5$, —SR$^5$, —CN, —SO$_2$R$^5$, —SO$_3$R$^5$, —SO$_2$NR$^5$R$^6$, or Ar;
R$^5$ and R$^6$ are each, independently, hydrogen, alkyl, alkenyl, alkynyl, or Ar;
Ar is phenyl, naphthyl, or hetaryl, wherein the foregoing may be optionally substituted; with the proviso that R and R$^1$ are both not hydrogen, or a pharmaceutically acceptable salt thereof which is useful as an immunosuppressive, antiinflammatory, antifungal, antiproliferative, and antitumor agent.

1 Claim, No Drawings

RAPAMYCIN AMIDINO CARBAMATES

This is a division of application Ser. No. 08/259,763 filed Jun. 14, 1994, now U.S. Pat. No. 5,463,048.

BACKGROUND OF THE INVENTION

This invention relates to amidino carbamates of rapamycin and a method for using them for inducing immunosuppression, and in the treatment of transplantation rejection, graft vs. host disease, autoimmune diseases, diseases of inflammation, adult T-cell leukemia/lymphoma, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], smooth muscle cell proliferation and intimal thickening following vascular injury [Morris, R. J. Heart Lung Transplant 11 (pt. 2): 197 (1992)], adult T-cell leukemia/lymphoma [European Patent Application 525,960 A1], and ocular inflammation [European Patent Application 532,862 A1].

Mono- and diacylated derivatives of rapamycin (esterified at the 28 and 43 positions) have been shown to be useful as antifungal agents (U.S. Pat. No. 4,316,885) and used to make water soluble aminoacyl prodrugs of rapamycin (U.S. Pat. No. 4,650,803). Recently, the numbering convention for rapamycin has been changed; therefore according to Chemical Abstracts nomenclature, the esters described above would be at the 31- and 42- positions. U.S. Pat. Nos. 5,118,678 and 5,302,584 discloses carbamates of rapamycin that are useful as immunosuppressive, antiinflammatory, antifungal, antiproliferative, and antitumor agents.

DESCRIPTION OF THE INVENTION

This invention provides derivatives of rapamycin which are useful as immunosuppressive, antiinflammatory, antifungal, antiproliferative, and antitumor agents having the structure

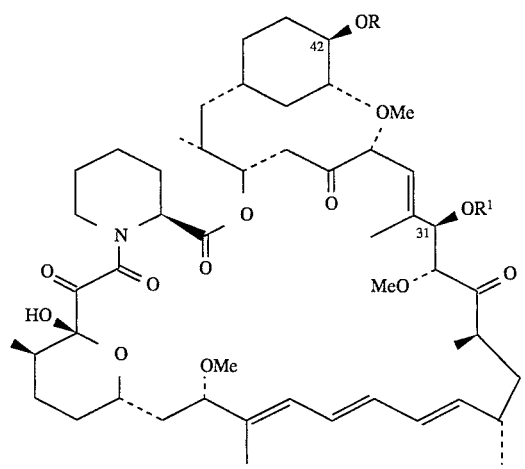

wherein R and $R^1$ are each, independently, hydrogen, or

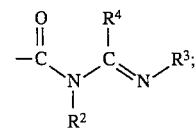

$R^2$ and $R^3$ are each, independently, hydrogen, alkyl of 1–6 carbon atoms, alkenyl of 2–7 carbon atoms, alkynyl of 2–7 carbon atoms, $-CO_2R^5$, $-COR^5$, $-CN$, $-NO_2$, $-SO_2R^5$, $-SO_3R^5$, $-OR^5$, $-SR^5$, or Ar;

$R^4$ is hydrogen, alkyl of 1–6 carbon atoms, alkenyl of 2–7 carbon atoms, alkynyl of 2–7 carbon atoms, $-CF_3$, $-NR^5R^6$, $-CO_2R^5$, $-COR^5$, $CONR^5R^6$, $-NO_2$, halogen, $-OR^5$, $-SR^5$, $-CN$, $-SO_2R^5$, $-SO_3R^5$, $-SO_2NR^5R^6$, or Ar;

$R^5$ and $R^6$ are each, independently, hydrogen, alkyl of 1–6 carbon atoms, alkenyl of 2–7 carbon atoms, alkynyl of 2–7 carbon atoms, or Ar;

Ar is phenyl, naphthyl, or hetaryl, wherein the foregoing may be optionally mono-, di-, or tri-substituted with a group selected from alkyl of 1–6 carbon atoms, alkenyl of 2–7 carbon atoms, alkynyl of 2–7 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, $-SO_3H$, and $-CO_2H$;

with the proviso that R and $R^1$ are both not hydrogen, or a pharmaceutically acceptable salt thereof.

The pharmaceutically acceptable salts are those derived from such inorganic cations such as sodium, potassium, and the like; organic bases such as: mono-, di-, and trialkyl amines of 1–6 carbon atoms, per alkyl group and mono-, di-, and trihydroxyalkyl amines of 1–6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The terms alkyl of 1–6 carbon atoms, alkenyl of 2–7 carbon atoms, and alkynyl of 2–7 carbon atoms, include both straight chain as well as branched carbon chains. When any of the generic terms (i.e., $R^5$) are contained more than once in a given compound, each may be the same or different.

Hetaryl is defined as an unsaturated or partially saturated heterocyclic radical of 5–12 atoms having 1 ring or 2 fused rings. Preferred heterocyclic radicals include unsaturated heterocyclic radicals such as furanyl, thiophenyl, pyrrolyl, pyrazolyl, imidazolyl, 1,2,3-triazolyl, 1,2,4-triazolyl, 1,2-dithiolyl, 1,3-dithiolyl, 1,2,3-oxathiolyl, isoxazolyl, oxazolyl, thiazolyl, isothiazolyl, 1,2,3-oxadiazolyl, 1,2,5-oxadiazolyl, 1,3,4-oxadiazolyl, 1,2,3,4-oxatriazolyl, 1,2,3,5-oxatriazolyl, 1,2,3-dioxazolyl, 1,2,4-dioxazolyl, 1,3,2-dioxazolyl, 1,3,4-dioxazolyl, 1,2,5-oxathiazolyl, 1,3-oxathiolyl, 1,2-pyranyl, 1,4-pyranyl, pyridinyl, pyridazinyl, pyrimidinyl, pyrazinyl, 1,3,5-triazinyl, 1,2,4-triazinyl, 1,2,3-triazinyl, 1,2,4-oxazinyl, 1,3,2-oxazinyl, 1,2,6-oxazinyl, 1,4-oxazinyl, isoxazinyl, 1,2,5-oxathiazinyl, 1,4-oxazinyl, o-isoxazinyl, p-isoxazinyl, 1,2,5-oxathiazinyl, 1,2,6-oxathiazinyl, 1,3,5,2-oxadiazinyl, azepinyl, oxepinyl, thiepinyl, 1,2,4-diazepinyl, benzofuranyl, isobenzofuranyl, thionaphthenyl, indolyl, indolenyl, 2-isobenzazolyl, 1,5-pyrindinyl, pyrano[3,4-b]pyrrolyl, benzpyrazolyl, benzisoxazolyl, benzoxazolyl, anthranilyl, 1,2-benzopyranyl, quinolinyl, isoquinolinyl, cinnolinyl, quinazolinyl, naphthyridinyl, pyrido[3,4-b]pyridinyl, pyrido[4,3-b]pyridinyl, pyrido[2,3-b]pyridinyl, 1,3,2-benzozazinyl, 1,4,2-benzoxazinyl, 2,3,1-benzoxazinyl, 3,1,4-benzoxazinyl, 1,2-benzisoxazinyl, 1,4-benzisoxazinyl, carbazolyl, purinyl, and partially saturated heterocyclic radicals selected from the list above. All of the preferred heterocyclic radicals contain at least one double bond. When the heterocyclic radical is partially saturated, one or more of the olefins in the unsaturated ring system is saturated; the partially saturated heterocyclic radical still contains at least one double bond. It is more preferred that hetaryl is pyridinyl.

Of the compounds of this invention preferred members are those in which $R^1$ is hydrogen.

Compounds of this invention having the amidino carbamate moiety at the 42- or 31,42-positions can be prepared by conversion of rapamycin to the 4-nitrophenylcarbonate (as illustrated in Example 1), followed by reaction with an appropriately functionalized amidine. Mixtures of 42- and 31,42-carbamates can be separated by chromatography.

The 31-amidino carbamates of this invention can be prepared by protecting the 42-alcohol of rapamycin with a protecting group, such as with a tert-butyl dimethylsilyl group, followed by carbamylation of the, 31-position by the procedures described above. The preparation of rapamycin 42-silyl ethers is described in U.S. Pat. No. B1 5,120,842, which is hereby incorporated by reference. Removal of the protecting group provides the 31-esterified compounds. In the case of the tert-butyl dimethylsilyl protecting group, deprotection can be accomplished under mildly acidic conditions, such as acetic acid/water/THF. The deprotection procedure is described in Example 15 of U.S. Pat. No. 5,118,678, which is hereby incorporated by reference.

Having the 31-position carbamylated and the 42-position deprotected, the 42-position can be carbamylated using a different amidine agent than was reacted with the 31-carbonate, to give compounds having different amidino carbamates at the 31- and 42- positions. Alternatively, the 42-carbamylated compounds, prepared as described above, can be converted to the 31-carbonate-42-carbamate and reacted with a different amidine to provide compounds having different carbamates at the 31- and 42-positions.

This invention also covers analogous carbamates of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023,262]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethylrapamycin under C.A. nomenclature]; and 15-hydroxyrapamycin [U.S. Pat. No. 5,102,876]. The disclosures in the above cited U.S. Patents are hereby incorporated by reference.

Immunosuppressive activity for representative compounds of this invention was evaluated in an in vitro standard pharmacological test procedure to measure the inhibition of lymphocyte proliferation (LAF) and in two in vivo standard pharmacological test procedures. The pinch skin graft test procedure measures the immunosuppressive activity of the compound tested as well as the ability of the compound tested to inhibit or treat transplant rejection. The adjuvant arthritis standard pharmacological test procedure, which measures the ability of the compound tested to inhibit immune mediated inflammation. The adjuvant arthritis test procedure is a standard pharmacological test procedure for rheumatoid arthritis. The procedures for these standard pharmacological test procedures are provided below.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An $IC_{50}$ was obtained for each test compound as well as for rapamycin. When evaluated as a comparator for the representative compounds of this invention, rapamycin had an $IC_{50}$ ranging from 0.4–1.0 nM. The results obtained are provided as an $IC_{50}$ and as the percent inhibition of T-cell proliferation at 0.1 μM. The results obtained for the representative compounds of this invention were also expressed as a ratio compared with rapamycin. A positive ratio indicates immunosuppressive activity. A ratio of greater than 1 indicates that the test compound inhibited thymocyte proliferation to a greater extent than rapamycin. Calculation of the ratio is shown below.

$$\frac{IC_{50} \text{ of Rapamycin}}{IC_{50} \text{ of Test Compound}}$$

Representative compounds of this invention were also evaluated in an in vivo test procedure designed to determine the survival time of pinch skin graft from male BALB/c donors transplanted to male $C_3H(H-2K)$ recipients. The method is adapted from Billingham R. E. and Medawar P. B., J. Exp. Biol. 28:385–402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days ±S.D.) of the drug treatment group was compared with the control group. The following table shows the results that were obtained. Results are expressed as the mean survival time in days. Untreated (control) pinch skin grafts are usually rejected within 6–7 days. Compounds were tested using a dose of 4 mg/kg.

The adjuvant arthritis standard pharmacological test procedure measures the ability of test compounds to prevent immune mediated inflammation and inhibit or treat rheumatoid arthritis. The following briefly describes the test procedure used. A group of rats (male inbread Wistar Lewis rats) are pre-treated with the compound to be tested (1 h prior to antigen) and then injected with Freud's Complete Adjuvant (FCA) in the right hind paw to induce arthritis. The rats are then orally dosed on a Monday, Wednesday, Friday schedule from day 0–14 for a total of 7 doses. Both hind paws are measured on days 16, 23, and 30. The difference in paw volume (mL) from day 16 to day 0 is determined and a percent change from control is obtained. The left hind paw (uninjected paw) inflammation is caused by T-cell mediated inflammation and is recorded in the above table (% change from control). The right hind paw inflammation, on the other hand, is caused by nonspecific inflammation. Compounds were tested at a dose of 5 mg/kg. The results are expressed as the percent change in the uninjected paw at day 16 versus control; the more negative the percent change, the more potent the compound. Rapamycin provided −90% change versus control, indicating that rapamycin treated rats had 90% less immune induced inflammation than control rats.

The results obtained in these standard pharmacological test procedures are provided following the procedure for making the specific compounds that were tested.

The results of these standard pharmacological test procedures demonstrate immunosuppressive activity both in vitro and in vivo for the compounds of this invention. The results obtained in the LAF test procedure indicates suppression of T-cell proliferation, thereby demonstrating the immunosuppressive activity of the compounds of this invention. Further demonstration of the utility of the compounds of this invention as immunosuppressive agents was shown by the results obtained in the skin graft and adjuvant arthritis standard pharmacological test procedures. Additionally, the results obtained in the skin graft test procedure further demonstrates the ability of the compounds of this invention to treat or inhibit transplantation rejection. The results obtained in the adjuvant arthritis standard pharmacological test procedure further demonstrate the ability of the compounds of this invention to treat or inhibit rheumatoid arthritis.

Based on the results of these standard pharmacological test procedures, the compounds are useful in the treatment or inhibition of transplantation rejection such as kidney, heart, liver, lung, bone marrow, pancreas (islet cells), cornea, small bowel, and skin allografts, and heart valve xenografts; in the treatment or inhibition of graft vs. host disease; in the treatment or inhibition of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation (including asthma, chronic obstructive pulmonary disease, emphysema, acute respiratory distress syndrome, bronchitis, and the like), and eye uveitis.

Because of the activity profile obtained, the compounds of this invention also are considered to have antitumor, antifungal activities, and antiproliferative activities. The compounds of this invention therefore also useful in treating solid tumors, adult T-cell leukemia/lymphoma, fungal infections, and hyperproliferative vascular diseases such as restenosis and atherosclerosis. When used for restenosis, it is preferred that the compounds of this invention are used to treat restenosis that occurs following an angioplasty procedure. When used for this purpose, the compounds of this invention can be administered prior to the procedure, during the procedure, subsequent to the procedure, or any combination of the above.

When administered for the treatment or inhibition of the above disease states, the compounds of this invention can be administered to a mammal orally, parenterally, intranasally, intrabronchially, transdermally, topically, intravaginally, or rectally.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

The compounds of this invention can be formulated neat or with a pharmaceutical carrier to a mammal in need thereof. The pharmaceutical carrier may be solid or liquid. When formulated orally, it has been found that 0.01% Tween 80 in PHOSAL PG-50 (phospholipid concentrate with 1,2-propylene glycol, A. Nattermann & Cie. GmbH) provides an acceptable oral formulation.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood sire am via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 µg/kg–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation and biological activities of representative compounds of this invention.

EXAMPLE 1

42-O-(4-Nitro-phenoxycarbonyl)rapmycin

To a solution of 5.15 g (5.633 mmol) of rapamycin in 40 ml of methylene chloride cooled to −78° C. with dry ice/acetone bath, was added 0.7 ml dry pyridine and 1.70 g (8.450 mmol) of p-nitrophenylchloroformate dissolved in 10 ml methylene chloride. The reaction mixture was allowed to warm to ambient and stirred overnight under nitrogen. The reaction mixture was concentrated in vacuo and partitioned between ether and water. The organic phase was washed with 0.1N HCl (3×), then with a saturated sodium chloride solution (2×), dried over magnesium sulfate, filtered and concentrated under vacuum to give a pale yellow solid. Purification by flash column chromatography (elution with 40% then 50% ethyl acetate/hexanes) gave 5.41 g (88%) of the title compound as a pale yellow solid.

$^1$H NMR (DMSO) δ 8.3 and 7.5 (d and d, aromatic-H, 4H), 4.5 (m, 42C-H, 1H).

MS (−) FAB m/z: 1078 (M$^-$), 590 (Southern Fragment).

EXAMPLE 2

Rapamycin 42-ester with (imino-phenyl-methyl)carbamic acid

To a solution of 1.0024 g (0.9287 mmol) of 42-O-(4-Nitrophenoxycarbonyl)rapamycin in 5 ml of DMF was added 0.2231 g (1.8574 mmol) of benzamidine. The reaction mixture was allowed to stir under nitrogen for 2 hours at ambient temperature, then was diluted with ethyl acetate and washed with portions of H$_2$O and brine. The organic phase was dried over magnesium sulfate, filtered and concentrated under vacuum to yield crude product. Purification by flash column chromatography (elution with 60% then 80% ethyl acetate/hexanes) gave 0.1032 g (10%) of the title compound as a pale yellow solid.

$^1$H NMR (DMSO) δ 9.05 (m, N-H, 2H), 7.98–7.48 (m, aromatic-H, 5H), 4.48 (m, 42C-H, 1H).

MS (−) FAB m/z: 1059 (M$^-$), 590 (Southern Fragment), 467 (Northern Fragment).

Results obtained in standard pharmacological test procedures:

LAF IC$_{50}$: 2.05 nM
LAF ratio: 0.47
Skin graft survival: 9.8±0.8
Percent change in adjuvant arthritis versus control: −91%

EXAMPLE 3

Rapamycin 42-ester with (imino-pyridin-2-yl)methyl)carbamic acid

To 0.585 g (3.7 mmol) of 2-amidinopyridine hydrochloride was added one equivalent of 0.1M sodium hydroxide/methanol after which the solvent was removed in vacuo. To the solution of the free base in 20 ml of DMF was added 4.0 g (3.7 mmol) of 42-O-(4-Nitro-phenoxycarbonyl)rapamycin. The reaction mixture was allowed to stir under nitrogen for 6 hours at ambient temperature, then was diluted with ethyl acetate and washed with portions of H$_2$O and brine. The organic phase was dried over magnesium sulfate, filtered and concentrated under vacuum to yield crude product. Purification by flash column chromatography (elution with 1:1 ethyl acetate: hexanes, then 100% ethyl acetate) gave 0.47 g (12%) of the title compound as an off-white solid.

$^1$H NMR (DMSO) δ 9.05 (m, N-H, 2H), 8.68–8.72 (m, Ar-H, 1H), 8.28–8.24 (m, Ar-H, 1H), 8.0–7.94 (m, Ar-H, 1H), 7.66–7.62 (m, Ar-H, 1H), 4.4 (m, 42C-H, 1H).

MS (−) FAB m/z: 1060 (M$^-$), 590 (Southern Fragment), 468 (Northern Fragment).

Results obtained in standard pharmacological rest procedures:

LAF IC$_{50}$: 0.60 and 0.55 nM

LAF ratio: 1.50 and 0.78
Skin graft survival: 11.7±1.0

What is claimed is:

1. A method of treating transplantation rejection graft vs. host disease in a mammal in need thereof, which comprises administering to said mammal an antirejection effective amount of a compound of the structure

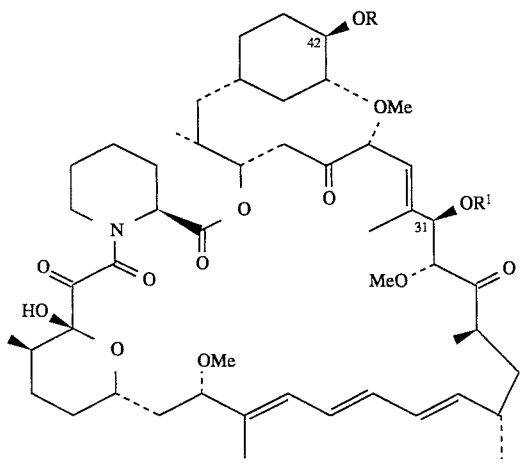

wherein R and $R^1$ are each, independently, hydrogen, or

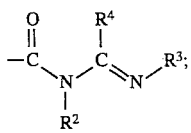

$R^2$ and $R^3$ are each, independently, hydrogen, alkyl of 1–6 carbon atoms, alkenyl of 2–7 carbon atoms, alkynyl of 2–7 carbon atoms, —$CO_2R^5$, —$COR^5$, —CN, —$NO_2$, —$SO_2R^5$, —$SO_3R^5$, —$OR^5$, —$SR^5$, or Ar;

$R^4$ is hydrogen, alkyl of 1–6 carbon atoms, alkenyl of 2–7 carbon atoms, alkynyl of 2–7 carbon atoms, —$CF_3$, —$NR^5R^6$, —$CO_2R^5$, —$COR^5$, $CONR^5R^6$, —$NO_2$, halogen, —$OR^5$, —$SR^5$, —CN, —$SO_2R^5$, —$SO_3R^5$, —$SO_2NR^5R^6$, or Ar;

$R^5$ and $R^6$ are each, independently, hydrogen, alkyl of 1–6 carbon atoms, alkenyl of 2–7 carbon atoms, alkynyl of 2–7 carbon atoms, or Ar;

Ar is phenyl, naphthyl, or hetaryl, wherein the foregoing may be optionally mono-, di-, or tri-substituted with a group selected from alkyl of 1–6 carbon atoms, alkenyl of 2–7 carbon atoms, alkynyl of 2–7 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, trifluoromethoxy, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —$SO_3H$, and —$CO_2H$;

hetaryl is a heterocyclic radical selected from the group consisting of furanyl, thiophenyl, pyrrolyl, pyrazolyl, imidazolyl, 1,2,3-triazolyl, 1,2,4-triazolyl, 1,2-dithiolyl, 1,3-dithiolyl, 1,2,3-oxathiolyl, isoxazolyl, oxazolyl, thiazolyl, isothiazolyl, 1,2,3-oxadiazolyl, 1,2,5-oxadiazolyl, 1,3,4-oxadiazolyl, 1,2,3,4-oxatriazolyl, 1,2,3,5-oxatriazolyl, 1,2,3-dioxazolyl, 1,2,4-dioxazolyl, 1,3,2-dioxazolyl, 1,3,4-dioxazolyl, 1,2,5-oxathiazolyl, 1,3-oxathiolyl, 1,2-pyranyl, 1,4-pyranyl, pyridinyl, pyridazinyl, pyrimidinyl, pyrazinyl, 1,3,5-triazinyl, 1,2,4-triazinyl, 1,2,3-triazinyl, 1,2,4-oxazinyl, 1,3,2-oxazinyl, 1,2,6-oxazinyl, 1,4-oxazinyl, isoxazinyl, 1,2,5-oxathiazinyl, 1,4-oxazinyl, o-isoxazinyl, p-isoxazinyl, 1,2,5-oxathiazinyl, 1,2,6-oxathiazinyl, 1,3,5,2-oxadiazinyl, azepinyl, oxepinyl, thiepinyl, 1,2,4-diazepinyl, benzofuranyl, isobenzofuranyl, thionaphthenyl, indolyl, indolenyl, 2-isobenzazolyl, 1,5-pyrindinyl, pyrano[3,4-b]pyrrolyl, benzpyrazolyl, benzisoxazolyl, benzoxazolyl, anthranilyl, 1,2-benzopyranyl, quinolinyl, isoquinolinyl, cinnolinyl, quinazolinyl, naphthyridinyl, pyrido[3,4-b]pyridinyl, pyrido[4,3-b]pyridinyl, pyrido[2,3-b]pyridinyl, 1,3,2-benzozazinyl, 1,4,2-benzoxazinyl, 2,3,1-benzoxazinyl, 3,1,4-benzoxazinyl, 1,2-benzisoxazinyl, 1,4-benzisoxazinyl, carbazolyl, and purinyl;

with the proviso that R and $R^1$ are both not hydrogen, or a pharmaceutically acceptable salt thereof.

* * * * *